(12) United States Patent
Almeida et al.

(10) Patent No.: US 9,556,482 B2
(45) Date of Patent: Jan. 31, 2017

(54) MOUSE CELL LINE AUTHENTICATION

(71) Applicant: United States of America as represented by the Secretary of Commerce, NIST, Washington, DC (US)

(72) Inventors: Jamie L. Almeida, Gaithersburg, MD (US); Kenneth D. Cole, Gaithersburg, MD (US)

(73) Assignee: The United States of America, as Represented by the Secretary of Commerce, Washington, DC (US)

( * ) Notice: Subject to any disclaimer, the term of this patent is extended or adjusted under 35 U.S.C. 154(b) by 483 days.

(21) Appl. No.: 13/935,285

(22) Filed: Jul. 3, 2013

(65) Prior Publication Data
US 2014/0066322 A1 Mar. 6, 2014

(51) Int. Cl.
*C12Q 1/68* (2006.01)

(52) U.S. Cl.
CPC ....... *C12Q 1/6881* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,599,666 | A | 2/1997 | Schumm et al. |
| 5,843,660 | A | 12/1998 | Schumm et al. |
| 6,156,512 | A | 12/2000 | Schumm et al. |
| 6,251,592 | B1 | 6/2001 | Tang et al. |
| 7,645,580 | B2 | 1/2010 | Barber et al. |
| 8,409,806 | B2 | 4/2013 | Green et al. |
| 2003/0180724 | A1 | 9/2003 | Schumm et al. |

(Continued)

FOREIGN PATENT DOCUMENTS

| EP | 0887426 A2 | 12/1998 |
| EP | 2010676 B1 | 1/2013 |

(Continued)

OTHER PUBLICATIONS

Almeida et al. (BMC Biotechnology, 2011, vol. 11, p. 1-10, IDS reference).*

*Primary Examiner* — Stephanie K Mummert

(74) *Attorney, Agent, or Firm* — Daphne Burton; Burton IP Law Group

(57) ABSTRACT

A multiplex polymerase chain reaction assay that targets nine tetranucleotide short tandem repeat (STR) markers in the mouse genome. Unique profiles were obtained from seventy-two mouse samples that were used to determine the allele distribution for each STR marker. Correlations between allele fragment length and repeat number were determined with DNA Sanger sequencing. Genotypes for L929 and NIH3T3 cell lines were shown to be stable with increasing passage numbers as there were no significant differences in fragment length with samples of low passage when compared to high passage samples. In order to detect cell line contaminants, primers for two human STR markers were incorporated into the multiplex assay to facilitate detection of human and African green monkey DNA. This multiplex assay is the first of its kind to provide a unique STR profile for each individual mouse sample and can be used to authenticate mouse cell lines.

10 Claims, 11 Drawing Sheets

(56) References Cited

U.S. PATENT DOCUMENTS

| | | |
|---|---|---|
| 2003/0224372 A1 | 12/2003 | Syndercombe-Court |
| 2004/0137452 A1 | 7/2004 | Levett et al. |
| 2006/0035236 A1 | 2/2006 | Keim et al. |
| 2006/0263785 A1 | 11/2006 | Quaife |
| 2009/0117542 A1 | 5/2009 | Maybruck et al. |
| 2010/0062430 A1 | 3/2010 | Hauzenberger et al. |
| 2010/0285463 A1 | 11/2010 | Kronenberg et al. |
| 2011/0171654 A1 | 7/2011 | Green et al. |
| 2011/0263437 A1 | 10/2011 | Fang et al. |
| 2011/0306505 A1 | 12/2011 | Chang et al. |
| 2012/0122093 A1 | 5/2012 | Hennessy et al. |

FOREIGN PATENT DOCUMENTS

| | | |
|---|---|---|
| WO | WO/99/14371 A1 | 3/1999 |
| WO | WO/99/61659 A1 | 12/1999 |
| WO | WO/01/92575 A1 | 12/2001 |
| WO | WO/02/068685 A2 | 9/2002 |
| WO | WO/03/102236 A1 | 12/2003 |
| WO | WO/2004/008841 A2 | 1/2004 |
| WO | WO/2009/003654 A2 | 1/2009 |
| WO | WO/2009/003654 A3 | 1/2009 |
| WO | WO/2011/032054 A2 | 3/2011 |
| WO | WO/2011/066467 A2 | 6/2011 |
| WO | WO/2011/133935 A2 | 10/2011 |
| WO | WO/2011/133947 A2 | 10/2011 |
| WO | WO/2012/067901 A1 | 5/2012 |

\* cited by examiner

| SEQ ID NO. | STR MARKER | GENBANK ACCESSION # | LOCATION ON CHROMOSOME (BP) | PRIMERS (5'-3') | PRIMER µM |
|---|---|---|---|---|---|
| 1 | 18-3 | NT_039674.8 | 60271556–60271705 | F:[FAM]-TCTTTCTCCTTTGTGTCATGC<br>R:GTTTCTTGCTAAATAACTAAGCAAGTGAACAGA | 0.200 |
| 2 | 4-2 | NT_187032.1 | 82068280–82068580 | F:[FAM]-AAGCTTCTCTGGCCATTTGA<br>R:GTTCATAAACTTCAAGCAATGACA | 0.125 |
| 3 | 6-7 | NT_039353.8 | 51601265–51601685 | F:[FAM]-AGTCCACCAGTGCATTCTC<br>R:GTTTCTTCATGTGGCTGGTATGCTGTT | 0.075 |
| 4 | 9-2 | NT_039474.8 | 74395400–74395000 | F:[VIC]-GGATTGCAAGAATTTGAGG<br>R:GTTTCTTCCTGAGTTGTGGACAGGGTTA | 0.080 |
| 5 | 15-3 | NT_039617.8 | 4930200–4930500 | F:[NED]-TCTGGGGTGTCTGTCATAA<br>R:GTTTCTTTTCTCAGGGAGGAGTGTGCT | 0.060 |
| 6 | 6-4 | NT_039360.8 | 142021975–142022270 | F:[NED]-TTTGCAACAGCTCAGTTTCC<br>R:GTTTCTTAATCGGTGGCAGATCTTAGG | 0.100 |
| 7 | 12-1 | NT_039548.8 | 384480950–38481170 | F:[PET]-CAAAATTGTCATTGAACACATGTAA<br>R:GTTTCTTCAATGGTCAAGAAATAGTGAAGTACAA | 0.200 |
| 8 | 5-5 | NT_109320.5 | 112641540–112641820 | F:[PET]-CGTTTTACTGGTCACACA<br>R:GTTTCTTCGGTTTAAAACTCAATACCAAACAA | 0.300 |
| 9 | X-1 | NT_039706.8 | 110959842–110960080 | F:[PET]-GGATGGATGGATGGATGAA<br>R:GTTTCTTAAGGTATATATCAAGATGGCATTATCA | 0.300 |
| 28 | D8S1106 | NT_167187.1 | 12835860–12836150 | F:[VIC]-GTTTTACCCTGCATCACTCG<br>R:GTTTCTTCAGAATTGCTCATAGTGCAAGA | 0.150 |
| 29 | D4S2408 | NT_006316.16 | 31304210–31304514 | F:[NED]-TCATTCATAGGGTAAGTGAAAA<br>R:GTTTCTTGCCATGGGATAAAATCAGA | 0.200 |

FIG. 1

SEQUENCING PRIMERS

| STR MARKER | PRIMERS (5'-3') | AMPLICON SIZE (bp) | T(Celsius) |
|---|---|---|---|
| 18-3 | 18-3 F: TCTTTCTCCTTTTGTGTCATGC<br>18-3 R: <u>G</u>TCAAAGTTGGGGTTACAGAATG* | 281-313 | 54 |
| 4-2 | 4-2 F: AAGCTTCTCTGGCCATTTGA<br>4-2 R: <u>G</u>TTCATAAACTTCAAGCAATGACA | 217-248 | 57 |
| 6-7 | 6-7 F: AGTCCACCCAGTGCATTCTC<br>6-7 R: <u>G</u>CATGTGGCTGGTATGCTGTT | 333-515 | 60 |
| 9-2 | 9-2 F: GGCTCTCTCACACCTCATCC*<br>9-2 R: <u>G</u>TCCATGAATCCAGACATTCC | 318-360 | 60 |
| 15-3 | 15-3 F: TCTGGGCGTGTCTGTCATAA<br>15-3 R: <u>G</u>TTCTCAGGGAGGAGTGTGCT | 157-222 | 60 |
| 6-4 | 6-4 F: TTTGCAACAGCTCAGTTTCC<br>6-4 R: <u>G</u>AATCGCTGGCAGATCTTAGG | 276-311 | 52 |
| 12-1 | 12-1 F: CAAAATTGTCATTGAACACATGTAA*<br>12-1 R: <u>G</u>CAATGGTCAAGAAATACTGAAGTACAA | 222-259 | 55 |
| 5-5 | 5-5 F: CGTTTTACCTGGCTGACACA<br>5-5 R: GATGCTTGCCTGTTCCTAGC | 258-298 | 60 |
| X-1 | X-1 F: GGATGGATGGATGGATGAAA<br>X-1 R: <u>G</u>AAGGTATATATCAAGATGGCATTATCA | 357-442 | 54 |

FIG. 2

DEFINING STR FRAGMENT LENGTH WITH CORRELATING REPEAT NUMBER

| STR | REPEAT MOTIF | ALLELE DISTRIBUTION AND CORRELATING FRAGMENT LENGTHS |
|---|---|---|
| 18-3 | [ATCT]n | 137 146 150 154 158 162 166 171 175 179<br>12.2 15 16 17 18 19 20 21 22 23 |
| 4-2 | [GATA]n[GATG]n[ATAG]n | 209 213 216 217 220 221 222 224 225 228 232 236 240 244 248<br>14 15 15.3 16 16.3 17 17.1 17.3 18 18.3 19.3 20.3 21.3 22.3 23.3 |
| 6-7 | [CTAT]n | 333 337 341 345 349 352 355 356 360 363 364 366 368 376 377 388<br>12 13 14 15 16 17 17.3 18 19 19.3 20 20.1 21 23 23.1 26 |
| 9-2 | [TAGA]n[AGAT]n | 188 192 204 219 220 223 227 231 235<br>7.1 8.1 11.1 15 15.1 16 17 18 19 |
| 15-3 | [TAGA]n | 157 165 169 177 181 184 189 193 196 200 204 208 212 216 220 222<br>12 14 15 17 18 18.3 19.3 20.3 21.3 22.3 23.3 24.3 25.3 26.3 27.3 28.1 |
| 6-4 | [ATAG]n[ATGA][TAGA]n | 276 285 286 289 290 293 294 297 298 301 302 307 311<br>11.2 13.3 14 14.3 15 15.3 16 16.3 17 17.3 18 19 20 |
| 12-1 | [AGAT]n[GATA]n | 222 226 227 230 231 234 235 238 239 242 246 247 250 254 259<br>15 16 16.1 17 17.1 18 18.1 19 19.1 20 21 21.1 22 23 24.1 |
| 5-5 | [TATC]n | 326 330 334 338 342 346 350 354 365<br>11 12 13 14 15 16 17 18 21 |
| X-1 | [ATAG]n[ATGA]n[TAGA]n | 380 385 389 393 397 401 404 405 409 413 421 428 448<br>20 21 22 23 24 25 25.3 26 27 28 30 32 37 |

FIG. 3

COMPLETE GENETIC PROFILES OF SIX MOUSE CELL LINES

| CELL LINE | ORIGIN | 18-3 | 4-2 | 6-7 | 9-2 | 15-3 | 6-4 | 12-1 | 5-5 | X-1 |
|---|---|---|---|---|---|---|---|---|---|---|
| NIH3T3 | NIH Swiss | 17, 19 | 19.3, 19.3 | 12, 12 | 15, 16 | 20.3, 20.3 | 14.3, 14.3 | 20, 20 | 14, 15 | 25, 25 |
| L-929 | C3H/An | 16, 16 | 20.3, 20.3 | 12, 12 | 15, 15 | 24.3, 25.3, 26.3 | 16, 16 | 16, 16 | 14, 14 | 26, 27 |
| MC3T3-E1 | C57BL/6 | 15, 15 | 20.3, 20.3 | 17, 17 | 17, 18 | 22.3 | 17, 17 | 17, 17 | 17, 17 | 28, 28 |
| RAW264.7 | Balb/c | 18, 18 | 22.3, 22.3 | 12, 12 | 15, 15 | 22.3, 22.3 | 17, 17 | 16, 16 | 14, 14 | 24, 24 |
| P3X63Ag8.653 | Balb/c | 18, 19 | 21.3, 21.3 | 12, 12 | 15, 16 | 22.3, 23.3 | 17, 18 | 16, 16 | 13, 14 | 25, 25 |
| HK-PEG-1 | Balb/c | 18, 19 | 21.3, 21.3 | 12, 12 | 15, 15 | 22.3, 23.3 | 17, 18 | 16, 16 | 13, 14 | 25, 25 |

FIG. 4

| MOUSE DNA SAMPLE | ORIGIN | MOUSE STR MARKERS | | | | | | | | |
|---|---|---|---|---|---|---|---|---|---|---|
| | | 18-3 | 4-2 | 6-7 | 9-2 | 15-3 | 6-4 | 12-1 | 5-5 | X-1 |
| CAST/EIJ | JL STOCK# 928 | OUT OF RANGE | 16 | 20 | 7.1 | 17 | 18 | 21.1 | 15 | 30 |
| MOLG/DN | JL STOCK# 555 | 20 | 17 | 23 | 7.1 | 17 | 18 | 19 | 14 | 32 |
| SWR/J | JL STOCK# 689 | 18 | 17.3 | 12 | 15 | 24.3 | 14.3 | 17 | 15 | 26 |
| 129P3/J | JL STOCK# 690 | 18 | 19.3 | 12 | 16 | 20.3 | 17 | 17 | 14 | 26 |
| 129S1/SVIMJ | JL STOCK# 2448 | 18 | 18.3 | 12 | 16 | 20.3 | 17 | 17 | 14 | 26 |
| BALB/CJ | JL STOCK# 651 | 17 | 21.3 | 12 | 15 | 21.3 | 17 | 16 | 13 | 25 |
| BUB/BNJ | JL STOCK# 653 | 17 | 19.3 | 12 | 15 | 20.3 | 16 | 18 | 15 | 26 |
| C3H/HEJ | JL STOCK# 659 | 16 | 19.3 | 12 | 15 | 26.3 | 18 | 16 | 15 | 27 |
| C57BL/6J | JL STOCK# 664 | 16 | 20.3 | 17 | 18 | 22.3 | 17 | 17 | 17 | 27 |
| C57L/J | JL STOCK# 668 | 16 | 18.3 | 15 | 15 | 18 | 17 | 17 | 17 | 26 |
| CBA/J | JL STOCK# 656 | 19 | 18.3 | 12 | 15 | 25.3 | 17 | 16 | 14 | 25 |
| DBA/1J | JL STOCK# 670 | 16 | 20.3 | 12 | 15 | 21.3 | 17 | 16 | 13 | 26 |
| I/LNJ | JL STOCK# 674 | 18 | 21.3 | 16 | 15 | 20.3 | 17 | 16 | 14 | 26 |
| KK/HLJ | JL STOCK# 2106 | 18 | 20.3 | 14 | 15 | 21.3 | 14.3 | 17 | 13 | 23 |
| LG/J | JL STOCK# 675 | 16 | 20.3 | 12 | 15 | 24.3 | 17 | 16 | 15 | 26 |
| LP/J | JL STOCK# 676 | 18 | 18.3 | 12 | 16 | 19.3 | 16.3 | 17 | 16 | 26 |
| LT/SVEI | JL STOCK# 3588 | 16 | 20.3 | 18 | 15 | 22.3 | 16 | 17 | 14 | 25 |
| NZB/BLNJ | JL STOCK# 684 | 22 | 19.3 | 14 | 15 | 21.3 | 15.3 | 18 | 12 | 24 |
| P/J | JL STOCK# 679 | 16 | 18.3 | 20 | 15 | 22.3 | 14.3 | 16 | 14 | 25 |
| PERC/EIJ | JL STOCK# 1307 | 18 | 19.3 | 20 | 17 | 21.3 | 16.3 | 18 | 14 | 25 |

FIG. 9

| MOUSE DNA SAMPLE | ORIGIN | MOUSE STR MARKERS | | | | | | | | |
|---|---|---|---|---|---|---|---|---|---|---|
| | | 18-3 | 4-2 | 6-7 | 9-2 | 15-3 | 6-4 | 12-1 | 5-5 | X-1 |
| SM/J | JL STOCK# 687 | 20 | 18.3 | 12 | 15 | 25.3 | 14.3 | 16 | 14 | 26 |
| WSB/EIJ | JL STOCK# 1145 | 19 | 20.3 | 14 | 16 | 18.3 | 17.3 | 16 | 14 | 21 |
| A/J | JL STOCK# 646 | 18 | 21.3 | 12 | 15 | 22.3 | 17 | 16 | 16,17 | 27 |
| NOD/SHILTJ | JL STOCK# 1976 | 18 | 18.3 | 14 | 15 | 22.3 | 15.3 | 17 | 15 | 26 |
| NZO/HLLTJ | JL STOCK# 2105 | 19 | 19.3 | 19 | 15 | 22.3 | 16,17 | 17 | 12 | 24 |
| PWK/PH | JL STOCK# 3715 | 19 | 19.3 | 15 | 7.1 | 15 | 15 | 16.1,17.1 | 15 | 20 |
| CD1/ICR MALE | ZYAGEN#GM-150M | 17 | 19.3 | 12,15 | 15 | 21.3 | 14.3,16 | 17,18 | 15 | 25 |
| CD1/ICR FEMALE | ZYAGEN#GM-150F | 17 | 18.3 | 12,15 | 15 | 22.3,23.3 | 16 | 19 | 14,15 | 25.3 |
| AKR/J | JL STOCK# 648 | 17 | 20.3 | 17 | 15 | 20.3 | 17 | 16 | 11 | 26 |
| ALR/LT | JL STOCK# 3070 | 22 | 19.3 | 12 | 15 | 20.3 | 17.3 | 21 | 15 | 27 |
| BTBR T<+>TF/J | JL STOCK# 2282 | 19 | 19.3 | 12 | 15 | 23.3 | 17.3 | 16 | 17 | 28 |
| C58/J | JL STOCK# 669 | 16 | 20.3 | 15 | 15 | 22.3 | 14.3 | 18 | 16 | 25 |
| CE/J | JL STOCK# 657 | 21 | 16.3 | 16 | 16 | 20.3 | 17 | 15 | 13 | 24 |
| CZECHI/EIJ | JL STOCK# 2799 | 18 | 18.3 | 18 | 7.1 | 14 | 17 | 17.1 | 15 | 25.3 |
| FVB/NJ | JL STOCK# 1800 | 17 | 19.3 | 12 | 15 | 20.3 | 14.3 | 20 | 14 | 26 |
| JF1/MS | JL STOCK# 3720 | 23 | 17 | OUT OF RANGE | 7.1 | 17 | 18 | 21.1 | 18 | 32 |
| MA/MYJ | JL STOCK# 677 | 17 | 19.3,20.3 | 14 | 15 | 24.3 | 15.3 | 17 | 14 | 27 |
| MOLC/RK | JL STOCK# 731 | 16 | 17 | 13 | 7.1 | 17 | 18 | 24.1 | 18 | 32 |
| MOLF/EIJ | JL STOCK# 550 | 15 | 17 | 17 | 7.1 | 17 | 18 | 24.1 | 14 | 32 |
| MRL/MPJ | JL STOCK# 486 | 17 | 20.3 | 12 | 15 | 25.3 | 17 | 16 | 15 | 26 |

FIG. 9 (Cont.)

| MOUSE DNA SAMPLE | ORIGIN | MOUSE STR MARKERS ||||||||||
| --- | --- | --- | --- | --- | --- | --- | --- | --- | --- | --- |
| | | 18-3 | 4-2 | 6-7 | 9-2 | 15-3 | 6-4 | 12-1 | 5-5 | X-1 |
| MSM/MS | JL STOCK# 3719 | 18 | 18 | 26 | 7.1 | 17 | 20 | 18.1 | 21 | 37 |
| NON/SHILT | JL STOCK# 1290 | 17 | 20.3 | 15 | 15 | 22.3 | 14.3 | 16.1 | 13 | 25 |
| NOR/LTJ | JL STOCK# 2050 | 18 | 18.3 | 14 | 15 | 20.3 | 15.3 | 17 | 15 | 27 |
| NZW/LACJ | JL STOCK# 1058 | 17 | 17.3 | 15 | 15 | 22.3 | 17 | 18 | 11 | 25 |
| PL/J | JL STOCK# 680 | 18 | 19.3 | 12 | 15 | 22.3 | 17 | 16 | 14 | 26 |
| RIIIS/J | JL STOCK# 683 | 18 | 19.3 | 14 | 15 | 25.3 | 16 | 17 | 15 | 25 |
| SB/LEJ | JL STOCK# 269 | 16 | 18.3 | 13 | 16 | 20.3 | 17 | 17 | 17 | 26 |
| SEA/GNJ | JL STOCK# 644 | 18 | 21.3 | 12 | 15 | 23.3 | 17 | 17 | 15,16 | 28 |
| SJL/J | JL STOCK# 686 | 17 | 19.3 | 12 | 15 | 22.3 | 14 | 17 | 14 | 26 |
| SPRET/EIJ | JL STOCK# 1146 | OUT OF RANGE | OUT OF RANGE | 17.3 | 15.1 | OUT OF RANGE | 11.2 | 17.1 | 17 | 17.1 |
| NIH3T3 | ATCC#CRL-1658 | 17,19 | 19.3 | 12 | 15,16 | 20.3 | 14.3 | 20 | 14,15 | 25 |
| L929 | ATCC#CCL-1 | 16 | 20.3 | 12 | 15 | 24.3,25.3,26.3 | 16 | 16 | 14 | 26,27 |
| MC3T3-E1 SUBCL 4 | ATCC#CRL-2593 | 15 | 20.3 | 17 | 17,18 | 22.3 | 17 | 17 | 17 | 28 |
| W-20-17 | ATCC#CRL-2623 | 16,18 | 20.3,23.3 | 12,17 | 18 | 22.3 | 17 | 16,17 | 12,17 | 27 |
| HK-PEG-1 | ATCC#CCL-189 | 18,19 | 21.3 | 12 | 15 | 22.3,23.3 | 17,18 | 16 | 13,14 | 25 |
| P3X63AG8.653 | ATCC#CRL-1580 | 18,19 | 21.3 | 12 | 15,16 | 22.3,23.3 | 17,18 | 16 | 13,14 | 25 |
| RAW 264.7 | ATCC#TIB-71 | 18 | 22.3 | 12 | 15 | 22.3 | 17 | 16 | 14 | 24 |
| M. DUNNI | ATCC#CRL-2017 | 15 | 17.1 | 20.1,23.1 | 11.1 | 12 | NO AMPLIF | 17,19,21 | 13,16 | OUT OF RANGE |

FIG. 9 (Cont.)

MOUSE CELL LINE AUTHENTICATION

STATEMENT REGARDING FEDERALLY SPONSORED RESEARCH/DEVELOPMENT

The subject matter of this patent application was invented under the support of at least one United States Government contract. Accordingly, the United States Government may manufacture and use the invention for governmental purposes without the payment of any royalties.

CROSS-REFERENCE TO RELATED APPLICATIONS

The present application claims priority to provisional application Ser. No. 61/692,761, filed on or about Aug. 24, 2012, entitled "Mouse Cell Line Authentication" naming the same inventors as in the present application. The contents of this provisional application are incorporated by reference herein, the same as if fully set forth.

BACKGROUND OF THE INVENTION

Field of Invention

The present disclosure relates to cell lines and mouse strains, more particularly, to mouse cell line authentication.

Description of Related Art

Cell line authentication is becoming increasingly important. For example, cell line authentication is now required by some journals prior to publication. In some cases, cell line authentication may be mandatory before receiving funding from some granting agencies.

The Federal Drug Administration has also instituted a requirement for the authentication of cell lines used to produce pharmaceuticals. Methods are currently in place for authenticating human cell lines using multiplex PCR assays that target short tandem repeat (STR) markers in the human genome and are capable of generating a unique individual genotypic profile. Cell repositories may now genotype their human cell lines using at least eight human STR markers including a marker for amelogenin, the sex identification locus.

Large databases of STR profiles may be used to confirm genotypes of human cell lines. These databases may also be used to provide a record of previously misidentified or cross-contaminated human cell lines. The American Type Culture Collection (ATCC) website maintains an updated list of misidentified human cell lines. Although there are successful methods in place for human cell line authentication, methods for nonhuman cell lines are not well established.

Mouse cell lines are commonly used to study human genes and disease. Mouse cells may also be used in the biomanufacturing of recombinant proteins and may also function as feeder cells for embryonic stem cells.

In the prior art, there are a number of techniques used to identify mouse cell lines or mouse strains, including but not limited to microsatellite markers (simple sequence length polymorphism (SSLP) or STR markers), single nucleotide polymorphisms (SNPs), and species-specific primers. One of the most commonly used laboratory strains is the *Mus musculus domesticus* strain. This strain may be difficult to genotype due to many shared alleles as a result of extensive breeding.

There have been published reports of multiplexing mouse SSLPs post-PCR by pooling the amplified products to distinguish between different strains of inbred mice. However, most of the microsatellite markers that have been used for these purposes are dinucleotide in nature, mainly CA repeats, which may result in noisy stutter and have relatively high mutation frequencies when compared to tetranucleotide repeats. The reduced stutter associated with tetranucleotide repeats may allow for easier interpretation of single and mixed profiles.

There is a need for mouse cell line authentication based on tetranucleotide repeats, as opposed to microsatellite markers that are dinucleotide in nature.

Current methods may lack the resolution to differentiate between individual mice of the same subspecies. SNPs may be well-conserved between inbred mice of the same strain. Thus, it may be difficult to differentiate between interstrain mice using this method. Even an extensive array containing over 600,000 mouse SNPs may still be unable to identify individual mice within the same subspecies.

Species-specific primers may be used to determine the origin of species for cell lines. However, species-specific primers may lack specificity to identify at the individual level.

For human cell lines, practices have been adopted that are currently used to identify such cells. These practices are based on the detection of short tandem repeat (STR) markers. However, for the large volume of research that is performed using nonhuman cell lines (mouse, hamster, monkey, etc.), there are no STR marker assays that are able to uniquely and unequivocally identify a particular cell line.

There is further a need for a mouse cell line authentication assay that uniquely identifies cell lines at the individual level.

BRIEF SUMMARY OF DISCLOSURE

The present disclosure addresses the needs described above by providing a PCR assay for mouse cell line authentication. The present assay may be used to authenticate mouse cell lines resulting in unique profiles for individual mouse samples based on tetranucleotide repeats that are stable with high passage number in the two different cell lines tested.

In accordance with one embodiment of the present disclosure, a method is provided for determining the alleles present in a DNA sample. The method comprises obtaining a DNA sample to be analyzed; and selecting a set of STR marker loci of the DNA sample to be analyzed that can be amplified together in a multiplex amplification reaction, wherein the set of STR marker loci are selected from the group consisting of: 18-3, 4-2, 6-7, 9-2, 15-3, 6-4, 12-1, 5-5 and X-1.

The method further comprises providing a set of oligonucleotide primer pairs, wherein each oligonucleotide primer pair in the set flanks a single locus in the set of STR marker loci, and wherein each primer pair is capable of amplification of a single locus from the set of STR marker loci in a multiplex amplification reaction. The method also comprises co-amplifying the set of STR marker loci in a multiplex amplification reaction, wherein the product of the multiplex amplification reaction comprises a mixture of amplified alleles from each of the co-amplified loci in the set of STR marker loci. Finally, the method comprises evaluating the products of the co-amplification reaction to determine the alleles present at each of the loci analyzed in the set of STR marker loci within the DNA sample.

In accordance with another embodiment of the present disclosure, a kit is provided for determining the alleles present in a DNA sample to be analyzed. The kit comprises oligonucleotide primer pairs for co-amplifying a set of STR marker loci of at least one DNA sample to be analyzed. The set of loci comprises one or more of STR loci selected from the group consisting of STR marker loci 18-3, 4-2, 6-7, 9-2, 15-3, 6-4, 12-1, 5-5 and X-1.

These, as well as other objects, features and benefits will now become clear from a review of the following detailed description of illustrative embodiments and the accompanying drawings.

BRIEF DESCRIPTION OF DRAWINGS

FIG. 1 is a table illustrating primers for STR amplification and their corresponding chromosomal locations in accordance with the present disclosure.

FIG. 2 is a table illustrating sequencing primers and their respective amplicon size range as well as annealing temperatures in accordance with the present disclosure.

FIG. 3 is a table defining STR fragment length and corresponding repeat number in accordance with the present disclosure.

FIG. 4 is a table illustrating the complete genetic profiles of six mouse cell lines in accordance with the present disclosure.

FIG. 9 is a table containing the STR profiles showing the allele ranges for the markers from mouse cell lines, mouse strains, and wild mice.

DEFINITIONS

Figure 5:
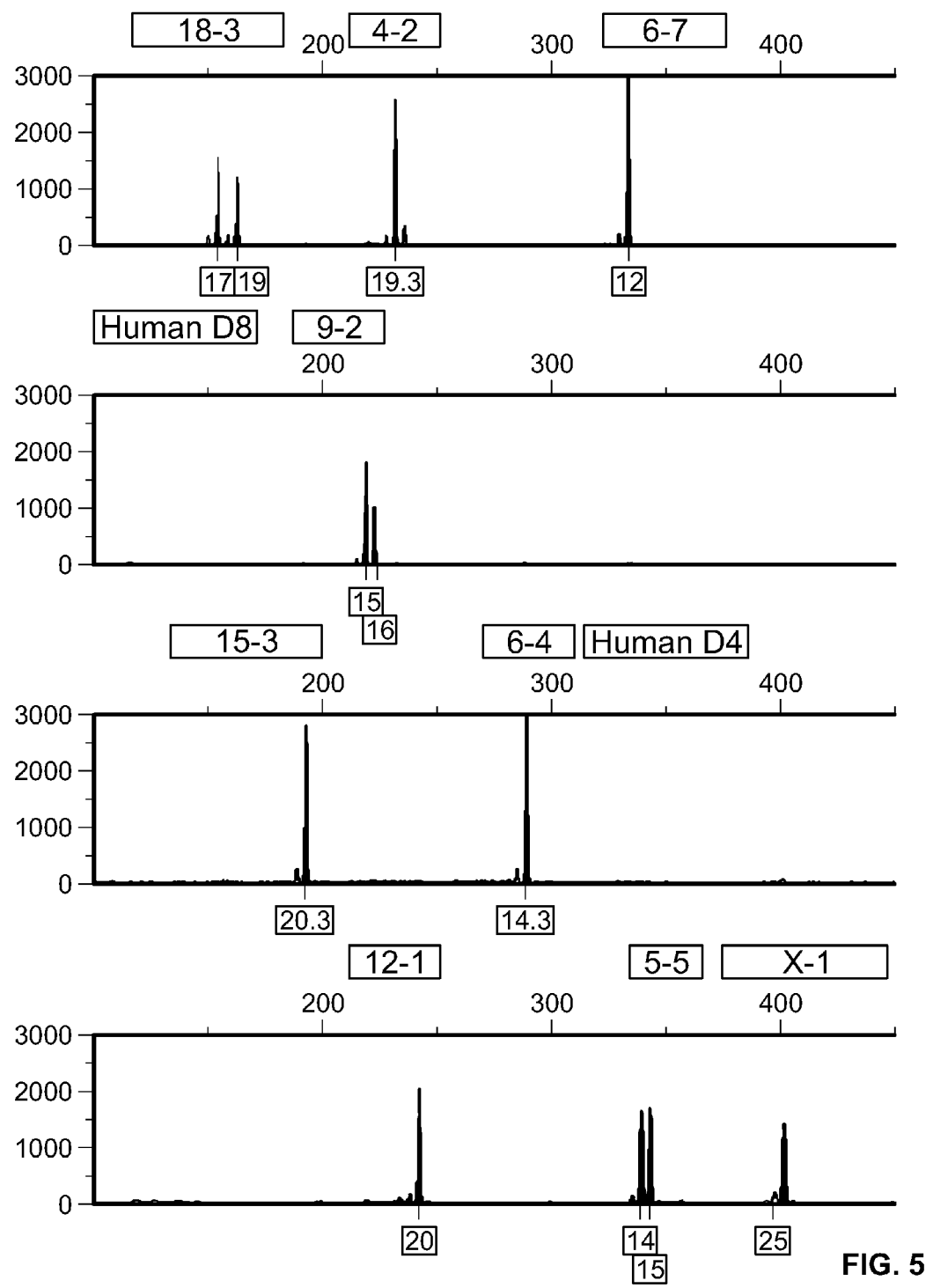
FIG. 5 is a genetic profile of an NIH3T3 cell line using the multiplex assay of the present disclosure.

Allele: The term "allele" as used herein refers to a genetic variation associated with a gene or a segment of DNA, i.e., one of two or more alternate forms of a DNA sequence occupying the same locus.

Amplicon/amplification product/amplified sequence: The terms "amplicon," "amplification product" and "amplified sequence" are used interchangeably herein and refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" and "amplified sequence" includes products from any number of cycles of amplification reactions.

Amplify: As used herein, "amplify" refers to the process of enzymatically increasing the amount of a specific nucleotide sequence. This amplification is not limited to but is generally accomplished by PCR. As used herein, "denaturation" refers to the separation of two complementary nucleotide strands from an annealed state. Denaturation can be induced by a number of factors, such as, for example, ionic strength of the buffer, temperature, or chemicals that disrupt base pairing interactions. As used herein, "annealing" refers to the specific interaction between strands of nucleotides wherein the strands bind to one another substantially based on complementarity between the strands as determined by Watson-Crick base pairing. It is not necessary that complementarity be 100% for annealing to occur. As used herein, "extension" refers to the amplification cycle after the primer oligonucleotide and target nucleic acid have annealed to one another, wherein the polymerase enzyme catalyzes primer extension, thereby enabling amplification, using the target nucleic acid as a replication template.

Detecting: The terms "detecting" and "detection" are used in a broad sense herein and encompass any technique by which one can determine the presence of or identify a nucleic acid sequence. In some embodiments, detecting comprises quantitating a detectable signal from the nucleic acid, including without limitation, a real-time detection method, such as quantitative PCR ("Q-PCR"). In some embodiments, detecting comprise's determining the sequence of a sequencing product or a family of sequencing products generated using an amplification product as the template; in some embodiments, such detecting comprises obtaining the sequence of a family of sequencing products. In other embodiments detecting can be achieved through measuring the size of a nucleic acid amplification product.

Locus-specific allelic DNA size marker: The term "locus-specific allelic DNA size marker" as used herein refers to a nucleic acid size standard for one or more alleles for a particular STR locus or marker. Those of skill in the art may variably refer to this as an "allelic ladder." The allelic ladder serves as a reference standard and nucleic acid size marker for the amplified alleles from the locus. In some embodiments, the allelic ladder can comprise size standards for the alleles of different STRs. In some embodiments, the allelic ladder can be made of DNA. In some embodiments, the allelic ladder can be made of non-naturally occurring nucleic acid analogs. The different individual size standards within an allelic ladder can, in some embodiments, be labeled with a detectable label, e.g., a fluorophore. In some embodiments, the allelic ladder components are labeled with the same fluorophore. In some embodiments, the allelic ladder components are labeled with different fluorophores. The size standards can be selected to work for a specific pair (or pairs) of oligonucleotides primers. For example, if a first set of primers for marker X with a tetranucleotide repeat produces a 150 base pair amplicon corresponding to allele 1, the corresponding allelic ladder component will serve as a size standard for the 150 base amplicons; while a second pair of primers for marker X produces a 154 base pair amplicon corresponding to allele 2, the corresponding allelic ladder component will serve as a size standard for the 154 base amplicons. Thus different size standards for different size amplicons of the same marker are contemplated. The size standard for a given amplicon derived from a given allele may have nucleic acid base sequence that is the same or different than the nucleic acid base sequence of the amplicon or allele from which the amplicon is derived. For allele analysis in electrophoresis systems the size standard can be selected so as to have the same electrophoretic mobility as the amplicon of interest. Alternatively, in some embodiments, the size standard can be selected so as to have different electrophoretic mobility than the amplicon of interest, given an understanding of the predicable nature of the difference; the identity of the amplicons could be determined. For allele analysis in mass spectroscopy systems the size standard (weight/charge ratio, not electrophoretic mobility) can be selected so as to have the same signal as the amplicon of interest. Alternatively, in some embodiments, the size standard (weight/charge ratio, not electrophoretic mobility) can be selected so as to have the different separation properties than the amplicon of interest, given an understanding of the predicable nature of the difference, the identity of the amplicons could be determined.

Primer: The term "primer" refers to a polynucleotide (oligonucleotide) and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides (dNTPs) and the like.

Amplification Primer/Oligonucleotide primer: As used herein, the terms "amplification primer" and "oligonucleotide primer" are used interchangeably and refer to an oligonucleotide, capable of annealing to an RNA or DNA region adjacent a target sequence, and serving as an initiation primer for DNA synthesis under suitable conditions well known in the art. Typically, a PCR reaction employs an "amplification primer pair" also referred to as an "oligonucleotide primer pair" including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

STR Marker/STR Locus: As used herein the terms "STR marker" and "STR locus", and their plural forms, are used to describe one of a set of marker loci suitable for use in genotyping using the method of the present invention. In particular:

"18-3" refers to the STR marker on mouse chromosome 18, corresponding to base pairs 60271556-60271705 (NCBI 38.1 mouse build, corresponding to GenBank Accession # NT_039674.8) (SEQ ID NO: 1) (REPEAT MOTIF: [ATCT]n);

"4-2" refers to the STR marker on mouse chromosome 4, corresponding to base pairs 82068280-82068580 (NCBI 38.1 mouse build, corresponding to GenBank Accession # NT_187032.1) (SEQ ID NO: 2) (REPEAT MOTIF: [GATA]n[GATG]n[ATAG]n;

"6-7" refers to the STR marker on mouse chromosome 6, corresponding to base pairs 51601265-51601685 (NCBI 38.1 mouse build, corresponding to GenBank Accession # NT_039353.8) (SEQ ID NO: 3) (REPEAT MOTIF: [CTAT]n);

"9-2" refers to the STR marker on mouse chromosome 9, corresponding to base pairs 74395400-74395000 (NCBI 38.1 mouse build, GenBank Accession # NT_039474.8) (SEQ ID NO: 4) (REPEAT MOTIF: [TAGA]n[AGAT]n);

"15-3" refers to the STR marker on mouse chromosome 15, corresponding to base pairs 4930200-4930500 (NCBI 38.1 mouse build, GenBank Accession # NT_039617.8) (SEQ ID NO: 5) (REPEAT MOTIF: [TAGA]n);

"6-4" refers to the STR marker on mouse chromosome 6, corresponding to base pairs 142021975-142022270 (NCBI 38.1 mouse build, GenBank Accession # NT_039360.8) (SEQ ID NO: 6) (REPEAT MOTIF: [ATAG]n[ATGA]n [TAGA]n);

"12-1" refers to the STR marker on mouse chromosome 12, corresponding to base pairs 38480950-38481170 (NCBI 38.1 mouse build, GenBank Accession # NT_039548.8) (SEQ ID NO: 7) (REPEAT MOTIF: [AGAT]n[GATA]n);

"5-5" refers to the STR marker on mouse chromosome 5, corresponding to base pairs 112641540-112641820 (NCBI 38.1 mouse build, GenBank Accession # NT_109320.5) (SEQ ID NO: 8) (REPEAT MOTIF: [TATC]n); and "X-1" refers to the STR marker on mouse chromosome X, corresponding to base pairs 110959842-110960080 (NCBI 38.1 mouse build, GenBank Accession # NT_039706.8) (SEQ ID NO: 9) (REPEAT MOTIF: [ATAG]n[ATGA]n [TAGA]n).

Unless defined otherwise, all technical and scientific terms used herein have the same meaning as is commonly understood by one of ordinary skill in the art to which these teachings belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference. The citation of any publication is for its disclosure prior to the filing date and should not be construed as an admission that the present teachings are not entitled to antedate such publication by virtue of prior disclosure.

DETAILED DESCRIPTION OF THE DISCLOSURE

The present disclosure relates to a method and kit for mouse cell line authentication. The method and kit disclosed herein target tetranucleotide repeats in the mouse genome including primers that amplify nine mouse short tandem repeat (STR) markers. Based on unique profiles obtained from seventy-two (72) mouse samples, the allele distribution for each short tandem repeat (STR) marker was determined. Correlations between allele fragment length and repeat number were confirmed with sequencing. The STR markers may be stable up to passage forty-five in L929 and NIH3T3 cell lines as there were no significant differences in fragment length in samples of low passage when compared to high passage samples. Primer sets for two human STR markers were incorporated into the multiplex method and kit to facilitate detection of human cell line contaminants. Adoption of this simple method and kit would provide assurance in cell line identity for researchers and cell repositories. The method and kit provide a unique STR profile for each individual mouse sample and can be used to authenticate mouse cell lines.

Target STR markers were chosen for each chromosome, including the X and Y chromosomes, by searching for tetranucleotide repeat sequences (AGAT and TCTA) within the mouse genome using the National Center for Biotechnology Information (NCBI) BLAST program Primers were tested to meet three requirements. First, the locus must be present in every sample tested. Second, the locus must contain a tetranucleotide repeat. Third, primers for each marker must amplify products in a functional multiplex.

Two markers were located on mouse chromosome six; however, they were 90 megabases (Mb) apart and on opposite arms of the chromosome and were considered unlinked. In humans, markers that are over 50 Mb apart have been considered unlinked.

Two well-characterized human STR markers, D8S1106 and D4S2408, may be included in the multiplex kit (sometimes referred to hereinafter as an "assay"). These markers may be used to screen for contamination of mouse cell lines with human or African green monkey cell lines. Both human STR markers can be used to identify human and African green monkey cell lines (e.g., Vero cells).

Primer3 software, available online from the Massachusetts Institute of Technology, may be used to design PCR primers to flank the STR regions by inputting the downloaded mouse sequences from the NCBI BLAST program. The parameters for Primer3 were set to target primers with annealing temperatures of 60° C. AUTODIMER™ software was used to assess primer-dimer interactions and hairpin structures of possible primer combinations to be used in the multiplex. Forward primers were labeled with one of the following fluorescent dyes at the 5' end: 6FAM™ (blue), VIC™ (green), NED™ (yellow), or PET™ (red) (Applied Biosystems, Foster, Calif.). In some cases, an additional guanine base (G) or a "PIGtail" sequence (GTTTCTT) was added to the 5' end of the unlabeled reverse primers to promote complete adenylation.

Referring now to FIG. 1, illustrated is a table showing the primers used for STR amplification and their corresponding chromosomal locations. In FIG. 1, mouse chromosomal locations, or base pairs (bp), are based on NCBI BLAST 38.1 mouse build. Chromosomal locations for human STR markers D8S1106 and D4S2408 are based on the NCBI 37.3 human build. Primer concentrations in the rightmost column are final concentrations of forward and reverse primers in a 20 μL reaction volume. Primer concentrations were determined empirically based on peak height, DNA concentration and the number of cycles in the PCR program.

Based on FIG. 1, the exemplary amplification primers are set forth below. In order to specifically amplify the selected STR markers, the following oligonucleotide primer pairs were used, where "F" and "R" correspond to the forward and reverse primers respectively. The PCR is the product expected from amplification of the particular STR locus to which the oligonucleotide pair was directed.

```
18-3:
                                         (SEQ ID NO: 10)
F-TCTTTCTCCTTTTGTGTCATGC (SEQ ID NO: 11)
R-GTTTCTTGCTAAATAACTAAGCAAGTGAACAGA (SEQ ID NO: 1)
Primer 4-2:
                                         (SEQ ID NO: 12)
F-AAGCTTCTCTGGCCATTTGA (SEQ ID NO: 13)
R-GTTCATAAACTTCAAGCAATGACA (SEQ ID NO: 2)
Primer 6-7:
                                         (SEQ ID NO: 14)
F-AGTCCACCCAGTGCATTCTC
```

```
                                         (SEQ ID NO: 15)
R-GTTTCTTCATGTGGCTGGTATGCTGTT (SEQ ID NO: 3)
Primer 9-2:
                                         (SEQ ID NO: 16)
F-GGATTGCCAAGAATTTGAGG (SEQ ID NO: 17)
R-GTTTCTTTCCTGAGTTGTGGACAGGGTTA (SEQ ID NO: 4)
Primer 15-3:
                                         (SEQ ID NO: 18)
F-TCTGGGCGTGTCTGTCATAA (SEQ ID NO: 19)
R-GTTTCTTTTCTCAGGGAGGAGTGTGCT (SEQ ID NO: 5)
Primer 6-4:
                                         (SEQ ID NO: 20)
F-TTTGCAACAGCTCAGTTTCC (SEQ ID NO: 21)
R-GTTTCTTAATCGCTGGCAGATCTTAGG (SEQ ID NO: 6)
Primer 12-1:
                                         (SEQ ID NO: 22)
F-CAAAATTGTCATTGAACACATGTAA (SEQ ID NO: 23)
R-GTTTCTTTCAATGGTCAAGAAATACTGAAGTACAA (SEQ ID NO: 7)
Primer 5-5:
                                         (SEQ ID NO: 24)
F-CGTTTTACCTGGCTGACACA (SEQ ID NO: 25)
R-GTTTCTTGGTTTAAAACTCAATACCAAACAA (SEQ ID NO: 8)
Primer X-1:
                                         (SEQ ID NO: 26)
F-GGATGGATGGATGGATGAAA (SEQ ID NO: 27)
R-GTTTCTTAAGGTATATATCAAGATGGCATTATCA (SEQ ID NO: 9)
Primer D8S1106:
                                         (SEQ ID NO: 30)
F-GTTTACCCCTGCATCATGG (SEQ ID NO: 31)
R-GTTTCTTTCAGAATTGCTCATAGTGCAAGA (SEQ ID NO: 28)
Primer D4S2408:
                                         (SEQ ID NO: 32)
F-TCATTTCCATAGGGTAAGTGAAAA
```

R-GTTTCTTGCCATGGGGATAAAATCAGA (SEQ ID NO: 33)

Primer (SEQ ID NO: 29)

Genomic mouse DNA samples were obtained from Jackson Laboratories (Bar Harbor, Me., USA). These samples represent 48 common inbred strains used in the scientific community. The DNA included thirty-seven inbred mice DNA samples, one recombinant inbred mouse sample, and ten wild-derived mice DNA samples. DNA from 15 wild-caught mice (courtesy of Dr. Michael Nachman from the University of Arizona, USA) collected in Tucson, Ariz. was used for heterozygosity studies.

Genomic DNA from mouse (male and female CD1/ICR), hamster (Syrian golden hamster, Chinese hamster), rat (Fischer, Wistar, Sprague Dawley), gerbil, pig, baboon, rhesus, and cynomolgus monkey were obtained from Zyagen (San Diego, Calif.). TN1 cells (stably transfected green fluorescent protein (GFP) expressing cell line derived from the parent NIH3T3 line) were originally obtained from the American Type Culture Collection, Manassas, Va., in 2003. The following cell lines were obtained from The American Type Culture Collection (ATCC, Manassas, Va.): NIH3T3 (CRL-1658), L-929 (CCL-1), MC3T3-E1 subclone 4 (CRL-2593), RAW 264.7 (TIB-71), *M. dunni* (CRL-2017), P3X63Ag8.653 (CRL-1580), HK-PEG-1 (CCL-189), Vero (CCL-81), HeLa (CCL-2), and CHO-K1 (CCL-61).

DNA was quantified using the SYNERGY™ Mx plate reader and TAKE3™ plate (BioTek, Winooski, Vt., USA) at an absorbance of 260 nm. To study STR marker stability as passage number increased, duplicate 25 $cm^2$ tissue culture flasks of L929 cells were carried independently, and one million cells were harvested at passage numbers 2, 4, 9, 14, 19, 22, 26, 29, 31, 37, 41, and 44. Duplicate 25 $cm^2$ flasks were also carried for NIH3T3 cells which were carried independently, and one million cells were harvested from passage numbers 5, 7, 10, 15, 20, 23, 26, 32, 35, 40, 43, and 45.

PCR amplification was performed on a VERITI™ thermal cycler (Applied Biosystems). The reaction mixture of 20 µL final volume contained 1 ng of mouse DNA (or 5 ng to 10 ng of non-mouse DNA for specificity studies), 1× GENEAMP® PCR Gold buffer (Applied Biosystems), 2 mM $MgCl_2$ (Applied Biosystems), 250 µM dNTPs (USB Corporation, Cleveland, Ohio, USA), forward labeled and reverse primers (as shown in FIG. 1 hereinabove), 1U AMPLITAQ GOLD™ DNA Polymerase (Applied Biosystems), and 0.16 mg/mL non-acetylated BSA (Invitrogen). PCR conditions for the multiplex assay are as follows: denaturation for 11 min at 95° C., amplification for 30 cycles of 45 s at 94° C., 2 min at 59° C., and 1 min at 72° C., followed by an extension for 60 min at 60° C., and a final soak at 25° C.

Initial unlabeled primers and their respective PCR products were screened by using gel electrophoresis. PCR products (4 µL) were added to the Lonza 5× loading dye (1 µL), loaded onto a 2.2% agarose Flash Gel (Lonza) and run at 275 V for 5 min. Forward primers generating clean PCR products were ordered with a fluorescent dye at the 5' end and were tested in monoplex reactions with mouse DNA from Jackson Laboratories, Zyagen, and mouse cell lines. Multiplex reactions were then optimized by varying primer combinations, primer concentrations, DNA concentration, and PCR cycle number. To analyze monoplex and multiplex PCR products, samples were prepared by adding 1 µL of amplified product and 0.3 µL of GENESCAN™ 500 LIZ internal size standard (Applied Biosystems) to 8.7 µL of HI-DI™ formamide (Applied Biosystems) for separation on the 16-capillary ABI 3130xl Genetic Analyzer (Applied Biosystems). A five dye matrix was established under the G5 filter with dyes 6FAM, VIC, NED, PET, and LIZ. POP-4™ (Applied Biosystems) was used on a 36 cm capillary array (Applied Biosystems) with 1× ACE™ buffer (Amresco, Solon, Ohio, USA). Samples were injected electrokinetically for 10 s at 3 kV. The STR alleles were separated at 15 kV at a run temperature of 60° C. Data from the 3130xl genetic analyzer was analyzed using the GENEMAPPER™ ID-X v1.1 Software (Applied Biosystems). Bins and panels were created in GENEMAPPER™ ID-X based on fragment length data generated from the fifty-seven mouse profiles using fixed bin allele sizes to determine allele calls. The allele distribution range for the human STR markers (D8S1106 and D4S2408) was previously described and adjustments were made to the size range to take into account the "PIGtail" sequence that was added to the reverse primers. Calibration of repeat number to allele fragment length was determined by DNA sequencing.

Multiplex primers were used for sequencing STR markers, except for three loci (18-3, 9-2, and 12-1) where sequencing primers were used. Referring now to FIG. 2, illustrated are the forward and reverse primers used to sequence each of the nine STR markers. Also shown in FIG. 2 are the corresponding annealing temperatures and amplicon sizes for these markers.

At least four homozygous samples were sequenced for each STR locus to determine the corresponding number of repeats for each allele. The targeted repeat regions were amplified using 0.15 µM unlabeled forward and reverse primers using the PCR reaction specified herein in connection with PCR amplification with the following thermal cycling program: denaturation for 10 min at 95° C., amplification for 35 cycles of 1 min at 94° C., 1 min at 52-60° C. (annealing temperature specific to individual primers), and 1 min at 72° C., followed by an extension for 45 min at 60° C., and a final soak at 25° C. Samples were treated with 2 µL of EXOSAP-IT® PCR product cleanup (USB Corporation) per 5 µL of PCR product. This product cleanup was used to remove unincorporated primers and deoxyribonucleotide triphosphates (dNTPs) by incubating samples for 90 min at 37° C. followed by 20 min at 80° C. to inactivate the enzymes. Samples were then sent to Eurofins MWG Operon for sequencing using BIGDYE® Terminator v3.1 (Applied Biosystems). Resulting profiles were received after data analysis was performed by Eurofins MWG Operon.

Mixture samples containing genomic DNA extracted from NIH3T3, RAW264.7, and HeLa cells were analyzed to assess the capability of the multiplex assay to detect low levels of contamination in NIH3T3 cells. DNA from NIH3T3 and RAW264.7 cells were added to individual reactions with a final concentration of 1 nanogram (ng) of total DNA in the following ratios 1:1, 2:1, 3:1, 5:1, 7:1, 9:1, and 10:1. Reciprocal reactions were also prepared using DNA from RAW264.7 and NIH3T3 cells. The same procedure was repeated using DNA from NIH3T3 and HeLa cells, followed by reciprocal reactions with DNA from HeLa and NIH3T3 cells. PCR amplification and PCR product analysis are described above.

The heterozygosity (H) values were calculated by dividing the number of heterozygotes at a locus into the total number of individuals. The probability of identity (PI) was calculated by the summation of the square of the genotype frequencies. The probability of a random match (PM) for a full profile was calculated by multiplying the inverse of each genotype frequency for each marker. The coefficient of inbreeding (F), specifically the fixation in a subpopulation compared to the total population (FST) was determined by subtracting the average heterozygosity of the two subpopulations (wild-caught mice and inbred mice samples) from the total heterozygosity, divided by the total heterozygosity.

The mouse primers targeting tetranucleotide repeat markers in the multiplex PCR assay were designed based on the annotated mouse genome from NCBI build 38.1 of *Mus musculus* origin. Fifty-seven genomic mouse DNA samples were tested using the multiplex assay and the designated allele range was determined for each marker, and fragment lengths were correlated to actual number of repeats using sequence analysis.

Referring now to FIG. 3, illustrated is a table defining STR fragment length and corresponding repeat number in accordance with the present disclosure. In FIG. 4, fragment length in base pairs corresponds to apparent size based on LIZ GENESCAN® 500 size standard. The corresponding number of repeats are each shown just below the fragment length. The corresponding number of repeats was determined by the analysis of 57 mouse DNA samples. The correlation of the allele size and number of repeats was determined based on sequencing data.

The mouse samples were selected to represent the genetic diversity of the mouse family tree. To determine the specificity of the multiplex assay, DNA was tested from several different species and subspecies of mice, near neighbors, and non-mouse samples. A panel of 57 mouse genomic DNA samples representing species from *M. musculus musculus, M. musculus domesticus, M. musculus molossinus, M. musculus castaneus, M. spretus* (Spain), and *M. dunni* were tested with the multiplex PCR primers to determine assay robustness. Full unique profiles amplified in the designated allele range were obtained from the panel for all but the following samples: CAST/EiJ (*M. musculus castaneus*), JF1/Ms (*M. musculus molossinus*), SPRET (*M. spretus*), and *M. dunni* cell line. DNA from CAST and JF1 mice resulted in amplicons for each marker. However, the PCR product was outside of the designated allele range for the 18-3 and 6-7 loci, respectively. Sequencing the CAST mouse DNA revealed that this sample has conserved sequence flanking the repeat region. However, fifty-two ATCT repeats were observed at this locus. Thus, twenty-nine more repeats were observed at this locus than in the designated allele range.

Because of additional repeats present in the CAST mouse sample, the amplified product appears between STR markers 4-2 and 6-7. All *M. musculus molossinus* samples resulted in full profiles except for DNA from the JF1 mouse which amplified outside the designated allele range for marker 6-7. The additional thirty-two repeats that JF1 contains at the 6-7 locus may be explained in the origin of *Mus musculus molossinus*, a natural hybrid of *M. m. musculus* and *M. m. castaneus*, the latter shown to deviate from the designated allele range at marker 18-3.

DNA from the SPRET mouse (*M. spretus*) results in amplicons that fall outside the designated allele range for the following loci: 18-3, 4-2, 15-3, and X-1. The SPRET sample was sequenced at the 18-3 locus resulting in sixty-six repeats, eleven of which were GTCT repeats embedded within the defined ATCT repeat for this marker. DNA extracted from the *M. dunni* cell line does not amplify at the 6-4 STR marker and falls outside the designated allele range for X-1. Further analysis of DNA from *M. dunni* and SPRET was not continued as their profiles were incomplete using the multiplex assay. Interestingly, CAST and SPRET are mapped together in group 2 in a published mouse family tree. However, full profiles within the allele range are observed for the other members in that group including PERC (*M. m. domesticus*), MOLG (*M. m. molossinus*), and MOLF (*M. m. molossinus*).

A panel of rodent and porcine DNA (rat, hamster, gerbil, pig), human cell lines (HeLa, HEPM, SK-BR-3, MCF10A) and nonhuman primate DNA samples (Vero, COS-7, rhesus, baboon, cynomolgus monkey) were tested with the multiplex assay to determine assay specificity. None of these samples resulted in a complete profile using the primers targeting mouse STR markers. DNA from Wistar, Fischer, and Sprague-Dawley rats resulted in a single amplified product in the red dye channel; however, each sample resulted in an amplicon with a fragment length of 219 base pairs. Characteristic stutter peaks associated with polymerase slippage of repeat regions were absent in the rat samples. Lack of stutter peaks and identical amplicon sizes for each rat strain suggests the peak present is most likely a PCR artifact rather than amplification of a repeat region. Amplification products were absent for each mouse STR marker when DNA from human and African green monkey cell lines were tested. However, both cell lines amplified at the human STR markers (D8S1106 and D4S2408) present in the multiplex as expected. No significant amplicons were visible for pig, hamster, or gerbil DNA.

SNP assays, commonly used to type mouse strains, are efficient in discriminating between different strains of mice, but may not be ideal in differentiating between cell lines derived from the same substrain. SNPs are mostly bi-allelic markers whereas STR markers typically have greater than five alleles. Using the mouse multiplex assay, unique profiles were obtained for the mouse cell lines listed in FIG. 5 with the capability of distinguishing between three Balb/c-derived cell lines. FIG. 5 is a table illustrating the complete genetic profiles of six mouse cell lines in accordance with the present disclosure.

In FIG. 4, the repeat numbers are listed for each locus. Microvariants are indicated by a decimal point. As shown in FIG. 4, there are many conserved alleles between the three Balb/c-derived samples; however, there are sufficient differences resulting in unique profiles for each individual cell line. Two of the Balb/c-derived cell lines, mouse myeloma cells (P3X63Ag8.653) and hybridoma cells (HK-PEG-1), are very similar in their genotype, only varying by one allele at the 9-2 locus. The HK-PEG-f cell line was produced by fusing P3X63Ag8.653 (myeloma cells originating from a BALB/c mouse) with spleen cells from a BALB/c mouse, explaining why they share so many alleles. The myeloma cell line is heterozygous at the 9-2 locus whereas the hybridoma cell line is homozygous. To verify the presence of a null allele at the 9-2 marker, a panel of primers was tested with DNA from the hybridoma cells resulting in amplicons ranging from 132 to 244 base pairs (bp). Homozygote peaks were present in each sample, supporting the findings that these two cell lines differ by one allele at this marker.

To test assay sensitivity and determine the lower limits of detection, DNA from NIH3T3, HeLa, and Vero cell lines was diluted from 6 nanograms (ng) to 7.8 picograms (pg). A full profile for NIH3T3 cells was obtained using 62 pg of DNA but resulted in a loss of an allele at one mouse STR markers at 31 pg of DNA. The two human STR markers were also tested and resulted in peaks above the analytical threshold (50 relative fluorescent units) for HeLa and Vero cell lines using 62 and 187 pg of DNA, but resulted in allelic drop-out at 31 and 93 pg of DNA, respectively. In previous studies, higher concentrations of Vero cell DNA (6 ng) were needed to obtain an STR profile using human STR markers when compared to human DNA (0.5-1 ng). This is consistent with the higher concentrations of Vero DNA needed in this study to amplify efficiently using the human STR markers in the multiplex assay.

The multiplex assay described herein was designed to detect human or African green monkey cell line contamination of mouse cells by incorporating two human STR markers that amplify outside the designated allele ranges for the nine mouse STR markers. Mixture ratios ranging from 1:1 to 10:1 of NIH3T3 and HeLa DNA were tested to model contamination scenarios.

Referring now to FIG. 5, illustrated is a genetic profile of the NIH3T3 cell line using the multiplex assay of the present disclosure. An electropherogram depicting a pure NIH3T3 STR profile is shown in this FIG. 7.

Figure 6:
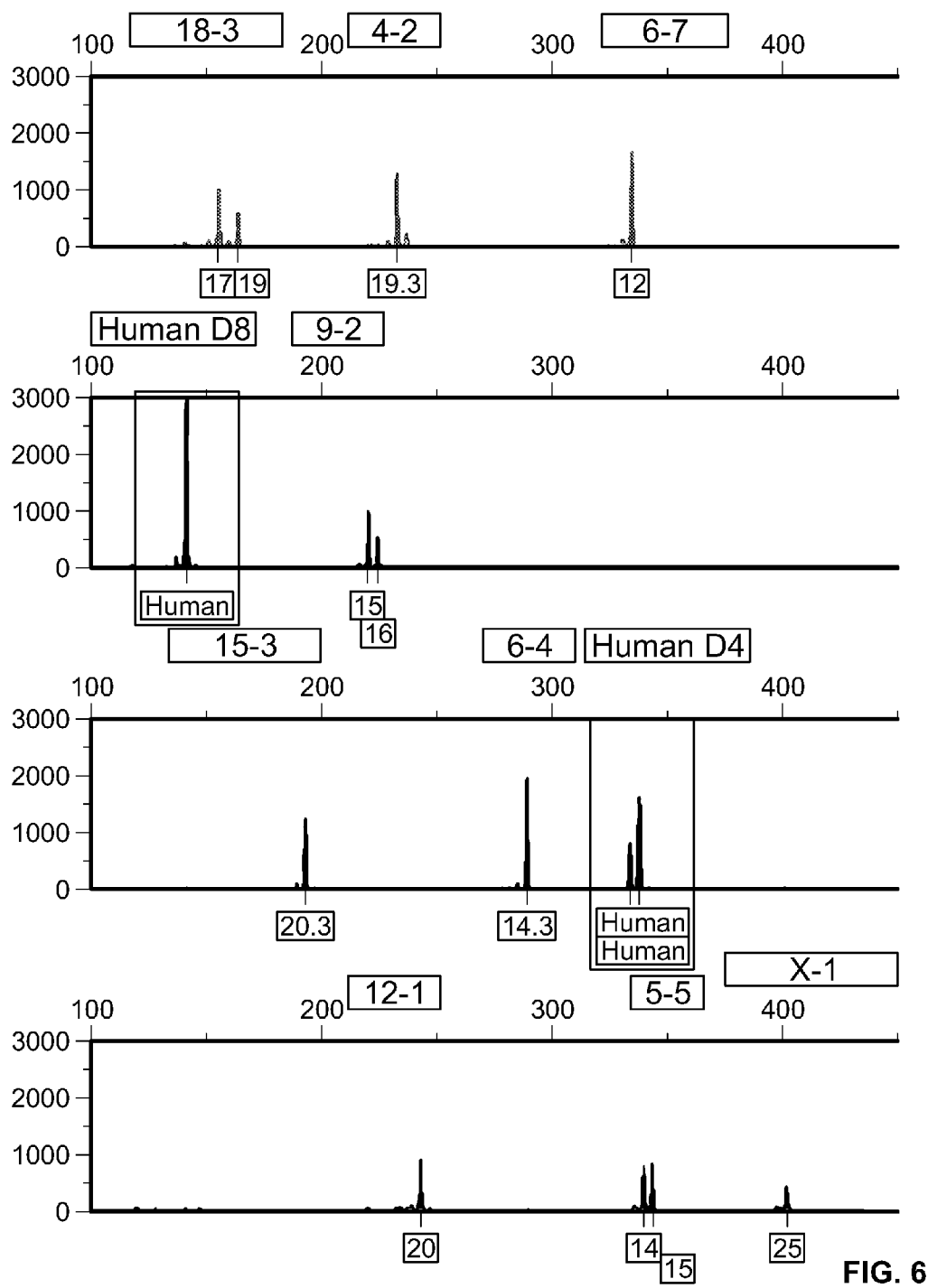
FIG. 6 illustrates the results obtained when a human contaminant is detected in an NIH3T3 STR profile in accordance with one embodiment of the present disclosure.

Referring now to FIG. 6, illustrated is a human contaminant detected in the NIH3T3 STR profile. A 1:1 ratio of NIH3T3 and HeLa DNA is shown in this FIG. 8. Even at the lowest dilution of HeLa DNA (90 pg), human STR markers were detected above the analytical threshold. The assay can also be used to detect a mixture of multiple mouse cell lines.

Figure 7:
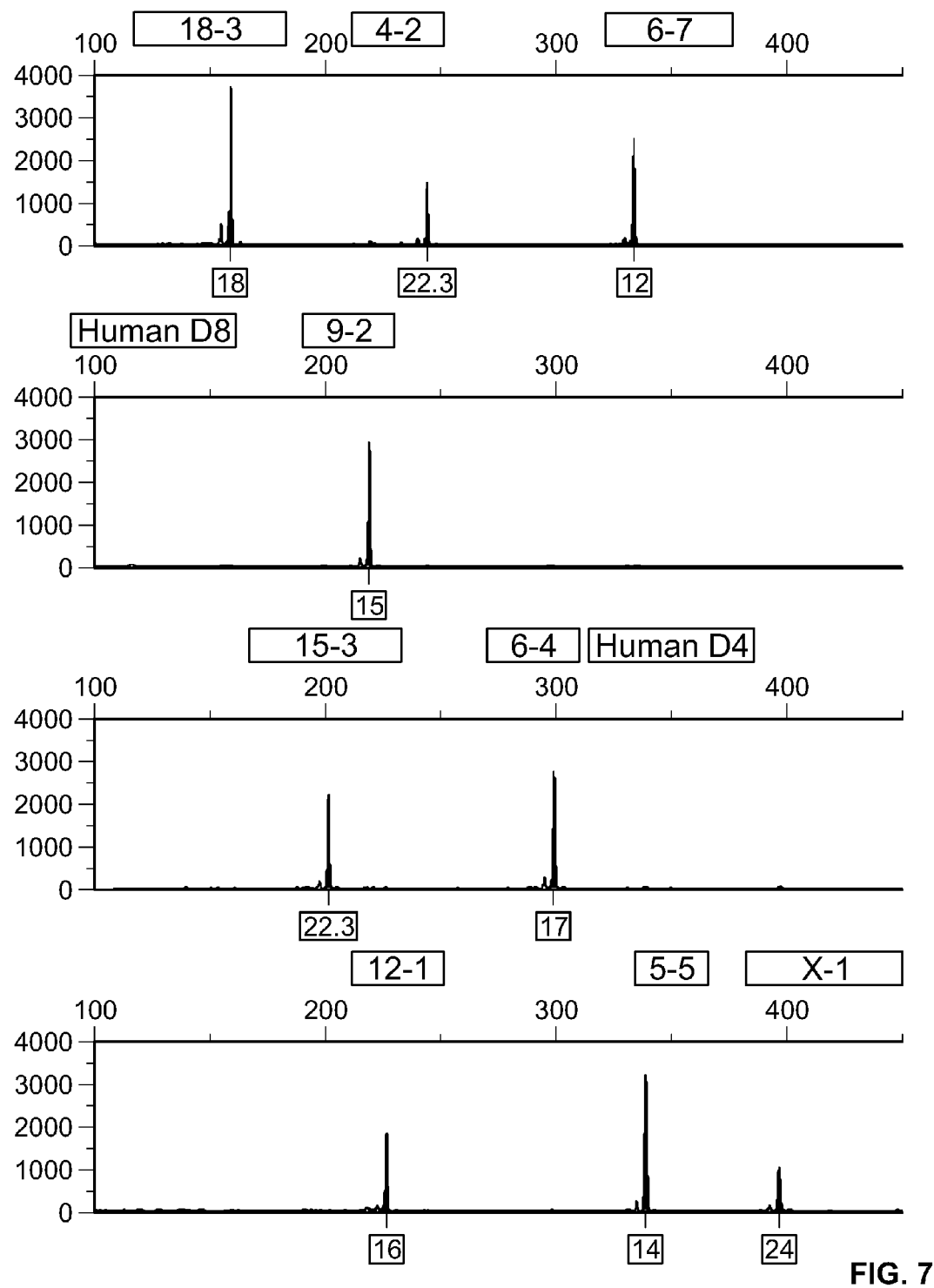
FIG. 7 is a genetic profile of a RAW 264.7 cell line using the multiplex assay of the present disclosure.

Referring now to FIG. 7, illustrated is a genetic profile of the RAW 264.7 cell line using the mouse multiplex assay (1 ng DNA). This electropherogram depicts a pure RAW264.7 STR profile. Mixture ratios ranging from 1:1 to 10:1 of NIH3T3 and RAW264.7 DNA were tested and full profiles of both cell lines were present even at the lowest DNA dilution (90 pg).

Figure 8:
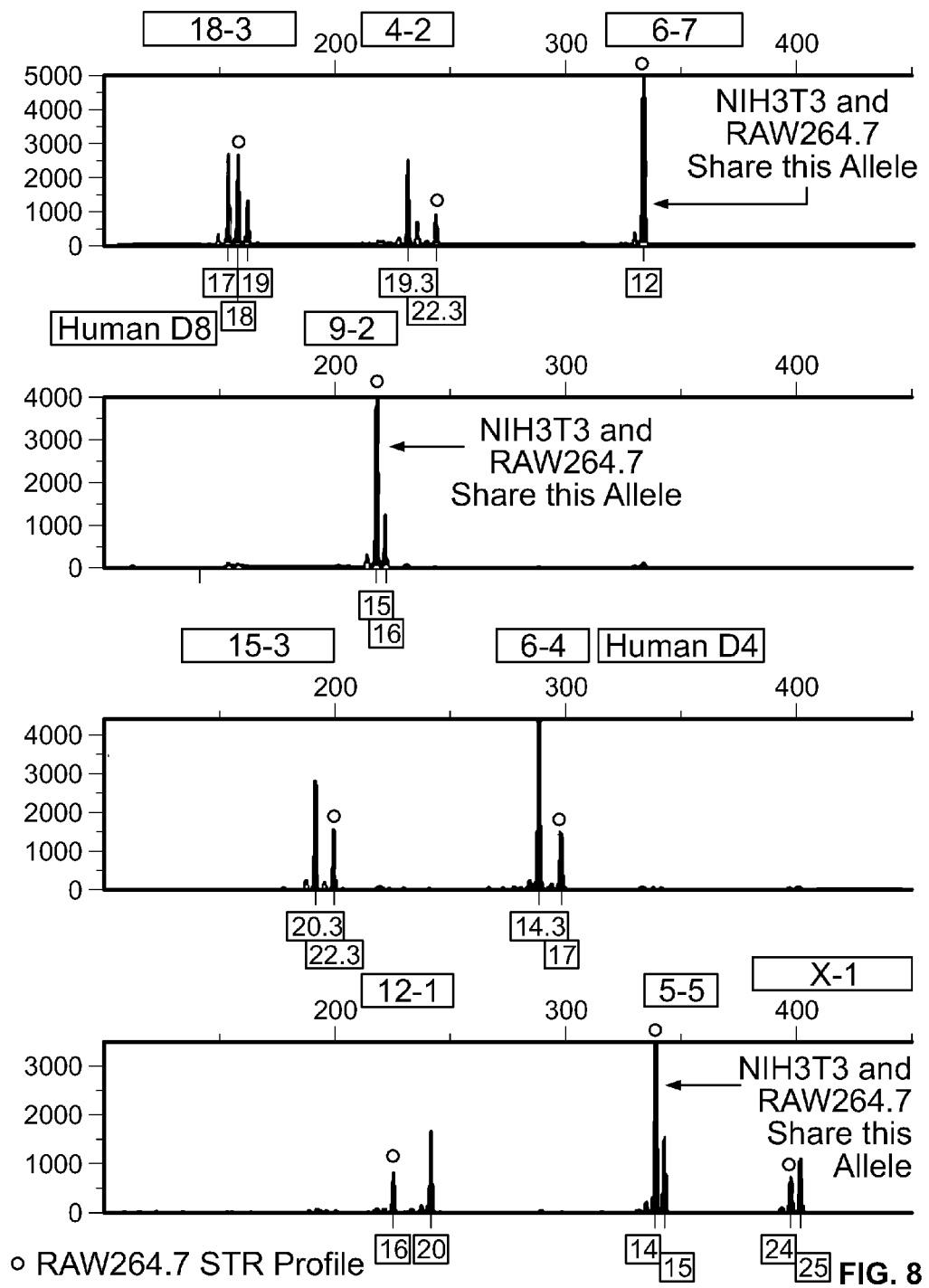
FIG. 8 is a mixture of NIH3T3 and RAW 264.7 cell lines detected using the multiplex assay of the present disclosure.

Referring now to FIG. 8, illustrated is a mixture of NIH3T3 and RAW 264.7 mouse cell lines detected using the assay described herein. FIG. 10 shows a 1:1 mixture of the two mouse cell lines.

The majority of mouse cell lines are derived from inbred mice resulting in alleles that are mostly homozygous in nature. For example, as shown earlier in connection with FIG. 4, the RAW 264.7 mouse cell line is homozygous at each STR marker. Multiple alleles present at each locus could indicate a mixed population of cells. Triallelic patterns have been observed in some human cell lines at a particular locus, which may or may not be equal in intensity. The L929 cell line appears to have three alleles with similar peak height intensities at the 15-3 marker and each allele is four base pairs or one repeat apart. Since most of the mouse samples tested were homozygous for the majority of the markers, a panel of primers targeting the 15-3 locus were tested in monoplex with DNA from L929 cells. The amplicons ranged from 210 to 435 base pairs in length and each resulted in three alleles that were four bases apart with very little peak height imbalance. The evidence supports a true triallelic pattern at the 15-3 marker.

Alteration of genetic profiles of some cancer cell lines has been observed previously at high passage numbers. However, other studies show STR stability over high passage numbers in some human cancer cell lines and in African green monkey cell lines. Accordingly, stability may be cell line dependent. To test the stability of the mouse STR markers in this assay, L929 and NIH3T3 cell lines were carried independently and in duplicate flasks up to passage 44 and 45, respectively.

Genotypes were determined and standard deviations were calculated for each locus representing the variations in fragment lengths over all passage numbers. The NIH3T3 cell line resulted in the lowest standard deviation values (0.02-0.05) for each locus. The L929 cell line resulted in standard deviations ranging from 0.05 to 0.14. The STR markers with the highest standard deviations in L929 cells are 6-7 (0.14) and 5-5 (0.13). In both the NIH3T3 and L929 cell lines, even the highest standard deviation values did not result in an allele repeat number change indicating stable STR profiles at high passage numbers. The changes in fragment lengths for each marker over the passage period were not significant enough to change the allele calls and the variability in the amplicon sizes fell within the range of the instrument fluctuation. Identical DNA samples were tested on three different days using the same instrument and the variation in fragment length was ±0.3 base pairs.

In addition to stability of the STR profile for NIH3T3 cells over time, profile stability was evaluated after transfection procedures. The TN1 cell line, derived from NIH3T3 cells obtained from ATCC in 2003 and engineered to express the gene for green fluorescent protein, was analyzed using the multiplex assay and resulted in identical STR profiles for both TN1 and recently obtained NIH3T3 cells. These data support the findings that the STR markers are stable over time in transfected NIH3T3 cell lines.

The mouse multiplex assay described herein can be used to identify cell lines derived from M. musculus musculus and M. musculus domesticus species. The assay is also useful in identifying M. musculus molossinus and M. musculus castaneus species which amplify at each locus, but in some instances failed to fall within the designated allele range for one of the STR markers. This assay may not be suitable for genotyping mouse cell lines derived from M. spretus (amplicons may fall outside the designated allele range for four STR markers) or M. dunni which may fail to amplify at the 6-4 locus.

Stability studies show the mouse STR markers are stable with high passage numbers and the STR profiles remain unchanged after transfection procedures in the TN1 cell line. Although the STR markers are stable up through passages 44-45, it may be desirable to genotype samples at low passage numbers. The power of discrimination based on the probability of a random match is 1 in 5.7 million using the nine STR markers in the multiplex assay. The assay described in the present disclosure can be used to identify both human and African green monkey cell line contaminants using the two human STR markers incorporated in the multiplex assay in addition to detecting mixtures of mouse cell lines. The targeted tetranucleotide repeat regions in the mouse genome result in unique individual profiles making this assay more sensitive and specific than those that are currently available. The requirement of cell line authentication is becoming more routine, and this assay provides a reliable method to genotype mouse cell lines.

The STR profiles shown in the Table in FIG. 9 display the allele range for the 9 markers. This data could be used to develop a size reference standard that is a locus-specific allelic ladder.

While the specification describes particular embodiments of the present invention, those of ordinary skill can devise variations of the present invention without departing from the inventive concept.

We claim:

1. A method of determining the alleles present in a DNA sample, the method comprising:
   obtaining a DNA sample to be analyzed;
   selecting a set of STR marker loci of the DNA sample to be analyzed that can be amplified together in a multiplex amplification reaction, wherein the set of STR marker loci are selected from the group consisting of: 18-3, 4-2, 6-7, 9-2, 15-3, 6-4, 12-1, 5-5 and X-1;
   providing a set of oligonucleotide primer pairs, wherein each oligonucleotide primer pair in the set flanks a single locus in the set of STR marker loci, and wherein each oligonucleotide primer pair is capable of amplification of a single locus from the set of STR marker loci in a multiplex amplification reaction;
   co-amplifying the set of STR marker loci in a multiplex amplification reaction, wherein the product of the multiplex amplification reaction comprises a mixture of amplified alleles from each of the co-amplified loci in the set of STR marker loci;
   evaluating the products of the co-amplification reaction to determine the alleles present at each of the loci analyzed in the set of STR marker loci within the DNA sample; and
   wherein the source of the DNA sample to be analyzed is at least one of a mouse and a cell line derived from a mouse.

2. The method of claim 1, wherein the mouse is selected from the group consisting of *Mus musculus musculus, Mus musculus domesticus, Mus musculus molossinus* and *Mus musculus castaneus*.

3. The method of claim 1, wherein the DNA sample to be analyzed comprises DNA derived from at least two different mouse sources.

4. The method of claim 1, wherein the DNA sample to be analyzed further comprises DNA derived from at least one other source that is a non-mouse source.

5. The method of claim 4, wherein the non-mouse source is at least one of human and African green monkey.

6. The method of claim 5, wherein the set of oligonucleotide primer pairs further comprises an oligonucleotide primer pair configured to amplify an STR allele from the non-mouse source.

7. The method of claim 1, wherein at least one oligonucleotide primer in each oligonucleotide pair comprises a detection label.

8. The method of claim 7, wherein the detection label comprises a fluorescent dye.

9. The method of claim 8, wherein evaluating the products of the co-amplification reaction comprises measuring fluorescence emission upon excitation of the detection label with light.

10. The method of claim 7, comprising using at least four oligonucleotide primer pairs, wherein at least one primer of each oligonucleotide primer pair is labeled with a detection label, and wherein at least four different detection labels are used.

* * * * *

SEQUENCE LISTING

<160> NUMBER OF SEQ ID NOS: 27

<210> SEQ ID NO 1
<211> LENGTH: 150
<212> TYPE: DNA
<213> ORGANISM: Mouse

<400> SEQUENCE: 1

```
tctttctcct tttgtgtcat gctaactcac aggtattttc tagatggttc catctatcta      60
tctatctatc tatctatcta tctatctatc tatctatcta tctatctatc tatctatcta     120
tatatctgtt cacttgctta gttatttagc                                      150
```

<210> SEQ ID NO 2
<211> LENGTH: 237
<212> TYPE: DNA
<213> ORGANISM: Mouse

<400> SEQUENCE: 2

```
aagcttctct ggccatttga agcatttctg tttgctatat tggttttact atatccaact      60
ggttttttcct agcttcagtg atgaaaatgg atagatagat agatagatag atagatagat    120
agatagatag atagatagat agatgataga tagatagata gatagatgat agagttctaa    180
tgcttataaa atgtgggtta caagaaaaat taaatgtcat tgcttgaagt ttatgaa       237
```

<210> SEQ ID NO 3
<211> LENGTH: 327
<212> TYPE: DNA
<213> ORGANISM: Mouse

<400> SEQUENCE: 3

```
agtccaccca gtgcattctc cagccagtgg agaagaggga gcgcaatggg gacaagtgcc      60
ttttaatttc tatttctttt gttgatgcct gcctgaatgt attctttcta tctatctatc    120
tatctatcta tctatctatc tatctatcta tctatcgtat gtgcatgtgt acgacacagc    180
tcatgtgtga aggtcagaag gcaactcccc gggagttggt tctttttttcc accatacaga   240
ttctggggaa ttaaagccat cttactggcc ccttagtttg tgtcttagca gcaagtttgg    300
atgacgtaac agcataccag ccacatg                                        327
```

<210> SEQ ID NO 4
<211> LENGTH: 228
<212> TYPE: DNA
<213> ORGANISM: Mouse

<400> SEQUENCE: 4

```
ggattgccaa gaatttgagg acagtctgtt tcaaatagtg agttttaggc cagcctgaaa      60
tattgatata ttgggatact gatacacatc tctagataga tagatagata gatagataga    120
tagatagata gatagataga tagatagata gaagatagat agataggcag acagaaaaat    180
cactgcctaa gagataaatg aaatgttaac cctgtccaca actcagga                 228
```

<210> SEQ ID NO 5
<211> LENGTH: 196
<212> TYPE: DNA
<213> ORGANISM: Mouse

<400> SEQUENCE: 5

```
tctgggcgtg tctgtcataa ataaggtagg agattagata gatagataga tagatagata      60
gatagataga tagatagata gatagatgat agatagatag atagatagat agatagatag    120
```

```
atagatgata gacagatata gatgagaaag aaagaaagaa atctatgcat gcattgagca    180
cactcctccc tgagaa                                                    196

<210> SEQ ID NO 6
<211> LENGTH: 294
<212> TYPE: DNA
<213> ORGANISM: Mouse

<400> SEQUENCE: 6
tttgcaacag ctcagtttcc ttgagaaaat tgctttaata caaatcccta ggaatctaca    60
tttctcctag gaaggtaatt tttagata gatagatgga gatagataga tagatagata     120
gatagataga tagatagata gatagataga tagatagatg atagatagat aaattctact    180
ggatagaaag atatcatgta ggctgagata ctacctactt atagtgaagt agtgaaggaa    240
attcataagc ggtaaataaa aagtattgga actacctaag atctgccagc gatt          294

<210> SEQ ID NO 7
<211> LENGTH: 224
<212> TYPE: DNA
<213> ORGANISM: Mouse

<400> SEQUENCE: 7
caaaattgtc attgaacaca tgtaaaaaag cagaagatag atagatagat agatagatag    60
atagatagat agatagatag atagatagat gatagataga tagatttatc taggagcata   120
gatgtaataa ctaaattgta taatgtgaca ttaaataagt ccatcactat aaaataatct   180
ttaataatta caaaaagttg tacttcagta tttcttgacc attg                    224

<210> SEQ ID NO 8
<211> LENGTH: 341
<212> TYPE: DNA
<213> ORGANISM: Mouse

<400> SEQUENCE: 8
cgttttacct ggctgacaca cttcctgggc cggtggctcc tggctttgaa agaaatcctt    60
gatggatgtc ataataaaga ggcttggtgg tgcggagcgc gaggatccgg gttccggttt   120
ctgcctttat ctatctatct atctatctat ctatctatct atctatctat ctatctatct   180
atctatctat ctatctatta tttatttatt caggaaatgc ttacttaggg agctgggtag   240
caaacaaggg ttttctgtac ctgctaggaa caggcaagca tccctaagtc agtttgtagt   300
ctttattaag caataaattg tttggtattg agttttaaac c                       341

<210> SEQ ID NO 9
<211> LENGTH: 402
<212> TYPE: DNA
<213> ORGANISM: Mouse

<400> SEQUENCE: 9
ggatggatgg atggatgaaa agaatagata gatagataga tagatagata gatagataga    60
tagatagata gatagataga tgatagatag atagatagat agatagatag atagatagat   120
agatagatag aaagaatgta atacatatga gcatactact cagttttaaa aattaatttc   180
tgccatttga tattattgac ctagaggaaa atatgttaca ttaaataacc tgtggaaatg    240
agtaggatac cacacaatcc catttaaatg ttttatatac atcttcactg ctcccgctgt   300
gacaaatagt gtccttattt ttgaatgttc taaaatattt tgttggttaa tattcattgt   360
```

```
acatagtcat gaatatgata atgccatctt gatatatacc tt        402
```

<210> SEQ ID NO 10
<211> LENGTH: 21
<212> TYPE: DNA
<213> ORGANISM: Mouse

<400> SEQUENCE: 10

```
tctttctcct ttgtgtcatg c                               21
```

<210> SEQ ID NO 11
<211> LENGTH: 33
<212> TYPE: DNA
<213> ORGANISM: Mouse

<400> SEQUENCE: 11

```
gtttcttgct aaataactaa gcaagtgaac aga                  33
```

<210> SEQ ID NO 12
<211> LENGTH: 20
<212> TYPE: DNA
<213> ORGANISM: Mouse

<400> SEQUENCE: 12

```
aagcttctct ggccatttga                                 20
```

<210> SEQ ID NO 13
<211> LENGTH: 24
<212> TYPE: DNA
<213> ORGANISM: Mouse

<400> SEQUENCE: 13

```
gttcataaac ttcaagcaat gaca                            24
```

<210> SEQ ID NO 14
<211> LENGTH: 20
<212> TYPE: DNA
<213> ORGANISM: Mouse

<400> SEQUENCE: 14

```
agtccaccca gtgcattctc                                 20
```

<210> SEQ ID NO 15
<211> LENGTH: 27
<212> TYPE: DNA
<213> ORGANISM: Mouse

<400> SEQUENCE: 15

```
gtttcttcat gtggctggta tgctgtt                         27
```

<210> SEQ ID NO 16
<211> LENGTH: 20
<212> TYPE: DNA
<213> ORGANISM: Mouse

<400> SEQUENCE: 16

```
ggattgccaa gaatttgagg                                 20
```

<210> SEQ ID NO 17
<211> LENGTH: 29
<212> TYPE: DNA
<213> ORGANISM: Mouse

<400> SEQUENCE: 17
gtttctttcc tgagttgtgg acagggtta                29

<210> SEQ ID NO 18
<211> LENGTH: 20
<212> TYPE: DNA
<213> ORGANISM: Mouse

<400> SEQUENCE: 18
tctgggcgtg tctgtcataa                20

<210> SEQ ID NO 19
<211> LENGTH: 27
<212> TYPE: DNA
<213> ORGANISM: Mouse

<400> SEQUENCE: 19
gtttcttttc tcaggagga gtgtgct                27

<210> SEQ ID NO 20
<211> LENGTH: 20
<212> TYPE: DNA
<213> ORGANISM: Mouse

<400> SEQUENCE: 20
tttgcaacag ctcagtttcc                20

<210> SEQ ID NO 21
<211> LENGTH: 27
<212> TYPE: DNA
<213> ORGANISM: Mouse

<400> SEQUENCE: 21
gtttcttaat cgctggcaga tcttagg                27

<210> SEQ ID NO 22
<211> LENGTH: 25
<212> TYPE: DNA
<213> ORGANISM: Mouse

<400> SEQUENCE: 22
caaaattgtc attgaacaca tgtaa                25

<210> SEQ ID NO 23
<211> LENGTH: 35
<212> TYPE: DNA
<213> ORGANISM: Mouse

<400> SEQUENCE: 23
gtttctttca atggtcaaga aatactgaag tacaa                35

<210> SEQ ID NO 24
<211> LENGTH: 20
<212> TYPE: DNA
<213> ORGANISM: Mouse

<400> SEQUENCE: 24
cgttttacct ggctgacaca                20

<210> SEQ ID NO 25
<211> LENGTH: 31
<212> TYPE: DNA
<213> ORGANISM: Mouse

-continued

```
<400> SEQUENCE: 25
gtttcttggt ttaaaactca ataccaaaca a                              31

<210> SEQ ID NO 26
<211> LENGTH: 20
<212> TYPE: DNA
<213> ORGANISM: Mouse

<400> SEQUENCE: 26
ggatggatgg atggatgaaa                                            20

<210> SEQ ID NO 27
<211> LENGTH: 34
<212> TYPE: DNA
<213> ORGANISM: Mouse

<400> SEQUENCE: 27
gtttcttaag gtatatatca agatggcatt atca                            34
```